United States Patent
Lantz et al.

[11] Patent Number: 5,836,930
[45] Date of Patent: Nov. 17, 1998

[54] ABSORBENT ARTICLE HAVING AN UMBILICAL PROTECTION FEATURE AND AN ABBREVIATED ABSORBENT STRUCTURE

[75] Inventors: Joanne Mary Lantz; David Louis Zenker, both of Neenah, Wis.; Thomas Harold Roessler, Menasha; Rob David Everett, Neenah; Lynn Carol Brud, Appleton; Barbara Ann Gossen, Neenah; Eric Mitchell Johns, Roswell; Cynthia Helen Nordness, Oshkosh, all of Wis.

[73] Assignee: Kimberly-Clark Worldwide, Inc, Neenah, Wis.

[21] Appl. No.: 284,728

[22] Filed: Aug. 2, 1994

Related U.S. Application Data

[63] Continuation of Ser. No. 53,531, May 3, 1993, abandoned.
[51] Int. Cl.⁶ ..................................................... A61F 13/15
[52] U.S. Cl. .................. 604/378; 604/385.1; 604/385.2; 604/389
[58] Field of Search .................................... 604/358, 378, 604/385.1–402

[56] References Cited

U.S. PATENT DOCUMENTS

| Re. 31,922 | 6/1985 | Mesek et al. | |
|---|---|---|---|
| 3,315,676 | 4/1967 | Cooper | 128/287 |
| 3,561,446 | 2/1971 | Jones, Sr. | 604/385.1 |
| 3,779,246 | 12/1973 | Mesek et al. | 128/287 |
| 3,995,637 | 12/1976 | Schaar | 604/385.2 |
| 4,037,602 | 7/1977 | Hawthorne | 604/385.1 |
| 4,094,319 | 6/1978 | Joa | 128/284 |
| 4,213,459 | 7/1980 | Sigl et al. | 128/287 |
| 4,333,782 | 6/1982 | Pieniak | 156/164 |
| 4,336,803 | 6/1982 | Repke | 604/385.2 |
| 4,337,771 | 7/1982 | Pieniak et al. | 128/287 |

(List continued on next page.)

FOREIGN PATENT DOCUMENTS

| 977268 | 11/1975 | Canada . |
|---|---|---|
| 1153152 | 9/1983 | Canada . |
| 1154901 | 10/1983 | Canada . |
| 1176401 | 10/1984 | Canada . |
| 1181201 | 1/1985 | Canada . |
| 1285702 | 7/1991 | Canada . |
| 0312071 | 4/1989 | European Pat. Off. . |
| 0320991 | 6/1989 | European Pat. Off. . |
| 0376022 | 7/1990 | European Pat. Off. . |
| 0433951 | 6/1991 | European Pat. Off. . |

OTHER PUBLICATIONS

Websters New International Dictionary, unabridged, p. 824, "elastic".
Grant & Hauch's Chemical Dictionary, p. 201, "elastomer" and p. 503, resilience.

*Primary Examiner*—Aaron J. Lewis
*Assistant Examiner*—K. M. Reichle
*Attorney, Agent, or Firm*—Paul Yee

[57] ABSTRACT

A distinctive absorbent article comprises a substantially liquid-impermeable outer cover member having a length and a width. The outer cover provides a rear waistband portion and a front waistband portion, and has a layer of polymer film material on an outer surface of the front waistband portion of the outer cover. A liquid permeable topsheet layer is provided for contacting a wearer's skin, and an absorbent body is interposed between the outer cover and the topsheet layer. The absorbent body has a length and width which are smaller than the outer cover length and width, thereby providing end margins and side margins of the outer cover. An adhesive fastening mechanism adheres to the film layer to secure the front and rear waistband portions of the outer cover about the wearer. An elastic member is connected to provide elasticized gathers along a cross-direction of the rear waistband portion of the outer cover. An outermost layer of substantially nonwettable, resilient material is connected to overlie the polymer film of the outer cover along the front waistband portion of the outer cover, thereby sandwiching the polymer film between the topsheet layer and the outermost layer of resilient material. The outermost resilient material has a lengthwise extent which is less than the length of the outer cover.

25 Claims, 6 Drawing Sheets

U.S. PATENT DOCUMENTS

| | | | |
|---|---|---|---|
| 4,388,075 | 6/1983 | Mesek et al. | 604/385 |
| 4,430,086 | 2/1984 | Repke | 604/385 |
| 4,475,912 | 10/1984 | Coates | 604/385 |
| 4,501,587 | 2/1985 | Enloe | 604/385 |
| 4,515,595 | 5/1985 | Kievit et al. | |
| 4,537,591 | 8/1985 | Coates | 604/391 |
| 4,548,604 | 10/1985 | Ellsworth | 604/399 |
| 4,578,066 | 3/1986 | O'Connor | 604/366 |
| 4,578,072 | 3/1986 | Lancaster | 604/385.1 |
| 4,585,448 | 4/1986 | Enloe | 604/378 |
| 4,681,581 | 7/1987 | Coates | 604/391 |
| 4,685,916 | 8/1987 | Enloe . | |
| 4,701,174 | 10/1987 | Johnson | 604/385.2 |
| 4,728,326 | 3/1988 | Gilles | 604/391 |
| 4,735,624 | 4/1988 | Mazars | 604/378 |
| 4,762,521 | 8/1988 | Roessler et al. | 604/385.1 |
| 4,769,024 | 9/1988 | Pike et al. | 604/390 |
| 4,773,906 | 9/1988 | Krushel | 604/391 |
| 4,801,298 | 1/1989 | Sorenson et al. | 604/384 |
| 4,861,652 | 8/1989 | Lippert et al. | 428/284 |
| 4,880,921 | 11/1989 | Widlund | 604/385.2 |
| 4,906,243 | 3/1990 | Dravland | 604/394 |
| 4,909,802 | 3/1990 | Ahr et al. | 604/385.1 |
| 4,938,754 | 7/1990 | Mesek | 604/385.2 |
| 4,981,480 | 1/1991 | Gaudet et al. | 604/386 |
| 4,997,428 | 3/1991 | Linnebur et al. | 604/368 |
| 5,034,008 | 7/1991 | Breitkopf | 604/385.2 |
| 5,057,097 | 10/1991 | Gesp | 604/389 |
| 5,064,421 | 11/1991 | Tracy | 604/385.1 |
| 5,069,672 | 12/1991 | Wippler et al. | 604/385.1 |
| 5,100,399 | 3/1992 | Janson et al. | 604/386 |
| 5,112,326 | 5/1992 | Quadrini | 604/391 | ial. The outermost resilient material has a lengthwise extent which is less than the length of the outer cover.
ABSORBENT ARTICLE HAVING AN UMBILICAL PROTECTION FEATURE AND AN ABBREVIATED ABSORBENT STRUCTURE This is a continuation of application Ser. No. 08/053,531 filed on May 3, 1993, now abandoned.

TECHNICAL FIELD

This invention relates to absorbent articles, particularly absorbent personal care products. More particularly, the invention relates to disposable garments which are worn by sensitive individuals, such as infants, and include a mechanism for selectively protecting or avoiding contact with tender regions of the body, such as the umbilical region of a newborn infant.

BACKGROUND OF THE INVENTION

Absorbent articles, such as disposable diapers, have included elasticized front and rear waistband sections which have been elasticized with soft elastic members composed of nonwoven fabric components. The soft nonwoven elastomeric members may be located on the outward surface or the bodyside surface of a substantially liquid impermeable polymer film backsheet layer, and may extend the total cross-directional widths of the waistband sections. For example, see U.S. Pat. No. 4,861,652 issued Aug. 29, 1989, to M. Lippert et al.

Conventional diapers have been configured with a transverse edge portions which can be folded along a fold line to provide a smaller diaper for newborn infants. For example, see U.S. Pat. Nos. 4,475,912 issued Oct. 9, 1984, to F. Coates; 4,537,591 issued Aug. 27, 1985, to F. Coates; 4,681,581 issued Jul. 21, 1987, to F. Coates; and 4,728,326 issued Mar. 1, 1988, to J. Gilles.

Other conventional, disposable diapers have incorporated a V-shape or U-shape notch cut away from the front waistband edge of the diaper to avoid contact with the umbilical cord region of a newborn infant.

Conventional diapers, such as those described above, have not, however, provided a desired combination of comfort and resistance to leakage. Structures that require complicated folding can be excessively difficult to configure on a moving infant, and typically employed materials have permitted excessive wicking of liquids out from the absorbent. Cutouts at the front waistband edge of the diaper have exhibited the problem of excessive wetness and/or leakage at the waistband. The edges of the cutouts can also excessively irritate the wearer's skin. As a result, there has been a continued need for improved structures which provide a desired combination of comfort and leakage resistance at the front waistband area of a disposable garment. More particularly, there has been a continued need for a diaper which avoids irritation around the sensitive umbilical cord of a newborn infant while still providing desired levels of leakage resistance.

BRIEF DESCRIPTION OF THE INVENTION

Generally stated, the present invention provides a distinctive absorbent article comprising a substantially liquid-impermeable outer cover member having a length and a width. The outer cover provides a rear waistband portion and a front waistband portion, and has a layer of polymer film material on an outer surface of at least the front waistband portion of the outer cover. The article includes a liquid permeable topsheet layer for contacting a wearer's skin, and an absorbent body interposed between the outer cover and the topsheet layer. The absorbent body has a length and width which are smaller than the outer cover length and width, thereby providing end margins and side margins of the outer cover. An adhesive fastening means is configured for adhering to the film layer to secure the front and rear waistband portions of the outer cover about the wearer. An elastic member connects to provide elasticized gathers along a cross-direction of the rear waistband portion of the outer cover. An outermost layer of substantially nonwettable, resilient material connects to overlie the polymer film of the outer cover along the front waistband portion of the outer cover, thereby sandwiching the polymer film between the topsheet layer and the outermost layer of resilient material. The outermost resilient material has a lengthwise extent which is less than the length of the outer cover.

Another aspect of the absorbent article of the invention comprises a substantially liquid-impermeable outer cover member having a length and a width, and providing a rear waistband portion and a front waistband portion. A liquid permeable topsheet layer contacts a wearer's skin, and an absorbent body is interposed between said outer cover and said topsheet layer. The absorbent body has a length and width which are smaller than said outer cover length and width, thereby providing end margins and side margins of said outer cover, and at least about 55 percent of an absorbent body length is located in a front half-section of the article. Fastening means secure the front and rear waistband portions of the outer cover layer about the wearer, and an elastic member is connected to provide elasticized gathers along a cross-direction of said rear waistband portion of said outer cover.

The various aspects of the absorbent article of the invention can advantageously provide a distinctive combination of comfort, absorbent efficiency and resistance to leakage. For example, the front waistband edge region of the article can be inwardly folded toward the wearer's skin to place the substantially nonwettable, resilient material against the wearer's skin, thereby reducing the length of the article and avoiding contact with the umbilical cord region of a newborn infant. The nonwettable material is soft and non-irritating to the wearer's skin while also providing resistance to the wicking and holding of liquids against the wearer's skin. In addition, the folded-over front waistband section can provide a substantially liquid impermeable barrier flap which resists the movement of liquid out from the absorbent body of the article.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The absorbent structures of the present invention will be described herein in relationship to their use in disposable absorbent articles, but it should be understood that potential uses of the absorbent structures of the present invention need not be limited to disposable absorbent articles. As used herein, the term "disposable absorbent article" refers to articles which absorb and contain body exudates and are intended to be discarded after a limited period of use. The articles are not intended to be laundered or otherwise restored for reuse. The articles can be placed against or in proximity to the body of the wearer to absorb and contain various exudates discharged from the body. While the present description will particularly be made in the context of a diaper article, it should be understood that the present invention is also applicable to other disposable personal care absorbent articles, such as adult incontinence garments, sanitary napkins, children's training pants and the like.

Figure 1:
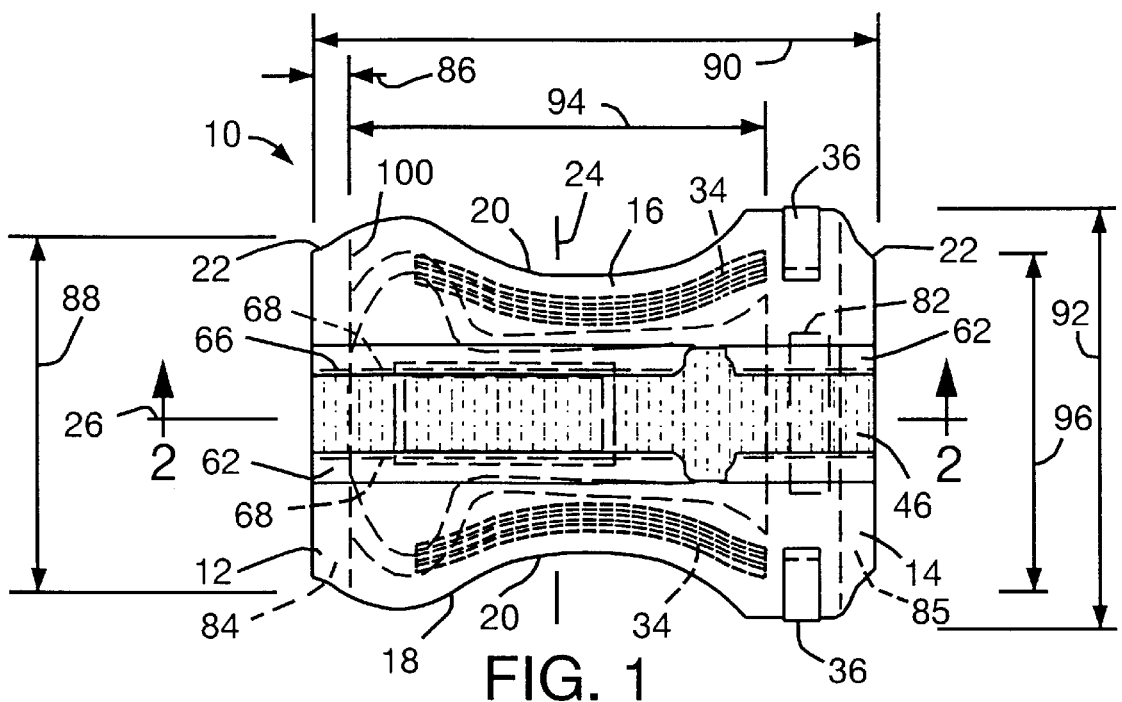
FIG. 1 representatively shows a top plan view of a fully extended diaper article of the invention.
Figure 2:
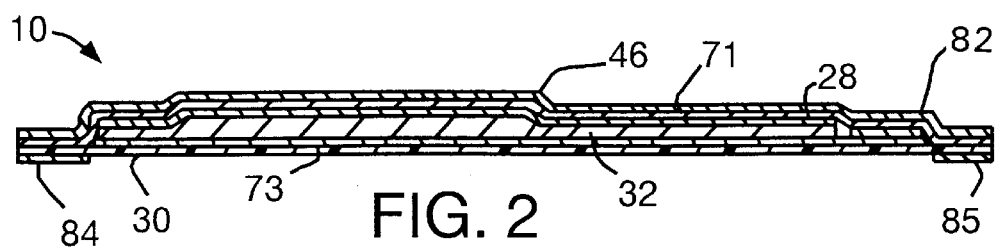
FIG. 2 representatively shows a cross-sectional view of a diaper article of the invention.
Figure 3:
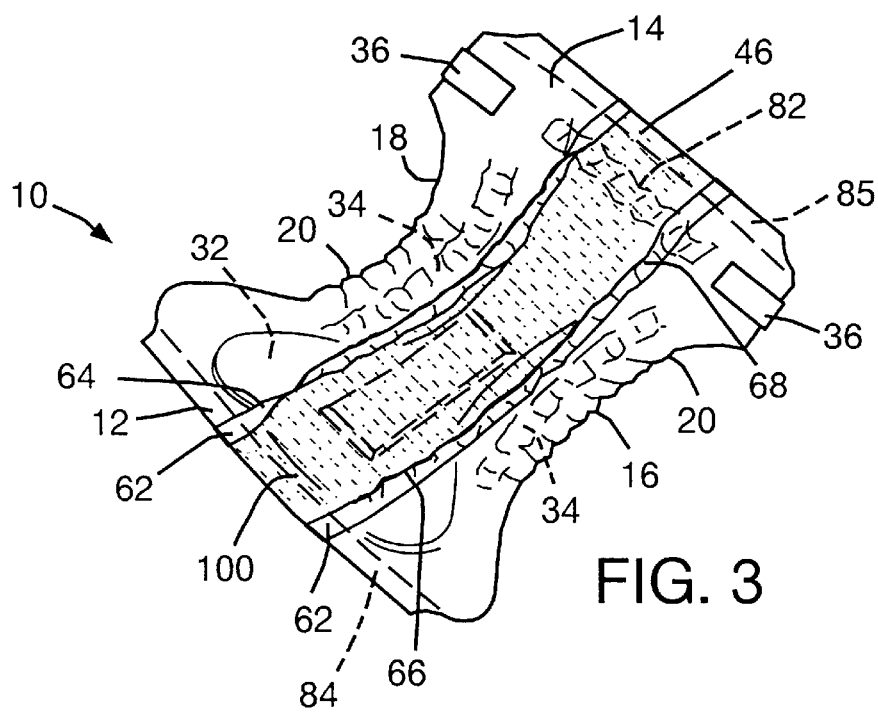
FIG. 3 representatively shows a perspective view of a diaper of the invention wherein the various elastics have contracted to gather elasticized sections thereof.

With reference to FIGS. 1 and 2, an absorbent article, such as diaper 10, is representatively shown in its extended, flat-out condition with all elastic contractions and gathers removed. Diaper 10 includes a substantially liquid-impermeable outer cover, such as backsheet layer 30, which in the shown embodiment, substantially defines a length 90 and a width 92 of the article. The outer cover provides a rear waistband portion 14 and a front waistband portion 12, and has a layer of polymer film material as an outer surface of at least the front waistband portion of the outer cover. In the illustrated embodiment, for example, a layer of substantially air-impermeable polymer film extends across substantially the entire outer surface of the outer cover. A liquid permeable topsheet layer 28 is positioned in a generally parallel, facing relation with backsheet 30, and is configured for contacting a wearer's skin. An absorbent body, such as absorbent structure 32, is interposed between backsheet 30 and topsheet 28. The absorbent body has a length 94 and a width 96 which are relatively smaller than the length and width of backsheet 30, thereby providing end margins 22 and side margins 20 of the outer cover backsheet. An adhesive fastening means, such as adhesive tape tabs 36, are configured for adhering to the film layer provided by backsheet 30 to secure the front and rear waistband portions 12 and 14 of backsheet 30 about the wearer. An elastic member 82 is connected to provide elasticized gathers along a cross-direction of rear waistband portion 14 of backsheet 30. An outermost layer of substantially nonwettable, resilient material, such as compressibly resilient patch 84 is connected to overlie the polymer film of backsheet 30 along the front waistband portion 12 of the backsheet, thereby sandwiching the polymer film between topsheet 28 and the outermost layer of resilient material 84. Resilient patch 84 has a lengthwise extent 86 which is less than the length 90 of backsheet 30.

Another aspect of the invention includes a substantially liquid-impermeable outer cover, such as backsheet layer 30, which can substantially define a length 90 and a width 92 of the article. The outer cover provides a rear waistband portion 14 and a front waistband portion 12. A liquid permeable topsheet layer 28 is positioned in a generally parallel, facing relation with backsheet 30, and is configured for contacting a wearer's skin. An absorbent body, such as absorbent structure 32, is interposed between backsheet 30 and topsheet 28, and has a length 94 and a width 96 which are relatively smaller than the length and width of the article, thereby providing end margins 22 and side margins 20 of the outer cover backsheet. The absorbent body is asymmetrically located along the length of the article delimited by backsheet 30, with at least about 55 percent of the absorbent body length located in a front half-section of the article. A fastening means, such as adhesive tape tabs 36, are configured for securing the front and rear waistband portions 12 and 14 of backsheet 30 about the wearer. An elastic member 82 is connected to provide elasticized gathers along a cross-direction of rear waistband portion 14 of backsheet 30.

In FIG. 1, portions of the structure are partially cut away to more clearly show the construction of diaper 10, and the side of the diaper which contacts the wearer is facing the viewer. The shown embodiment of diaper 10 has an intermediate crotch region 16 which interconnects the front and rear waistband regions 12 and 14. The outer edges of the diaper define a periphery 18 in which the longitudinally extending side edge margins are designated 20 and the laterally extending end edge margins are designated 22. Preferably, the side edges are curvilinear and contoured to define leg openings for the diaper. The end edges are shown as straight, but optionally, may be curvilinear. The diaper has a transverse center line 24 and a longitudinal center line 26.

Diaper 10 typically includes a liquid permeable topsheet 28; a substantially liquid impermeable backsheet 30; an absorbent body, such as absorbent structure 32, positioned between the topsheet and backsheet; and elastic members 34 and 82. Topsheet 28, backsheet 30, absorbent structure 32, and the elastic members 34 and 82 may be assembled in a variety of well-known diaper configurations.

The various aspects of the invention can further include a surge management portion 46. The surge management portion may be located on a bodyside surface 25 of topsheet 28 (FIG. 4), or alternatively, may be located on an outer side surface 27 of the topsheet (FIG. 5).

Absorbent article structures suitable for use with the present invention are described in U.S. patent application Ser. No. 07/757,778 of D. Proxmire et al., filed Sep. 11, 1991, and entitled "ABSORBENT ARTICLE HAVING A LINER WHICH EXHIBITS IMPROVED SOFTNESS AND DRYNESS, AND PROVIDES FOR RAPID UPTAKE OF LIQUID" (Attorney Docket No. 9932), the disclosure of which is hereby incorporated by reference to the extent that it is consistent with the present specification. Other absorbent article structures suitable for use with the present invention are described in U.S. patent application Ser. No. 07/757,760; "THIN ABSORBENT ARTICLE HAVING RAPID UPTAKE OF LIQUID"; of W. Hanson et al. (Attorney Docket No. 9922), the disclosure of which is hereby incorporated by reference to the extent that it is consistent herewith.

In the shown embodiment of diaper 10, topsheet 28 and backsheet 30 are generally coextensive and have length and width dimensions which are generally larger than the corresponding dimensions of absorbent structure 32. Topsheet 28 is associated with and superimposed on backsheet 30, thereby defining the periphery 18 of diaper 10. The periphery delimits the outer perimeter or the edges of the diaper 10, and in the illustrated embodiment, comprises end edges 22 and contoured longitudinal edges 20. The diaper 10 has front and back waistband regions 12 and 14, respectively extending from the laterally extending end edges 22 of diaper periphery 18 toward the transverse center line 24 of the diaper along a distance of from about 2 percent to about 10 percent and preferably about 5 percent of the length of diaper 10. The waistband regions comprise those upper portions of diaper 10, which when worn, wholly or partially cover or encircle the waist or mid-lower torso of the wearer. In particular aspects of the invention, backsheet 30 provides front and/or rear waistbands 12, 14 which are substantially impermeable to liquid. In other aspects of the invention, backsheet 30 provides front and/or rear waistbands 12, 14 which are substantially impermeable to air.

The intermediate, crotch region 16 lies between and interconnects waistband regions 12 and 14, and comprises that portion of diaper 10 which, when worn, is positioned between the legs of the wearer and covers the lower torso of the wearer. Thus, the crotch region 16 is an area where repeated fluid surge typically occur in diaper 10 or other disposable absorbent article.

Topsheet 28 presents a body-facing surface which is compliant, soft-feeling, and non-irritating to the wearer's skin. Further, topsheet 28 can be less hydrophilic than retention portion 48, and is sufficiently porous to be liquid permeable, permitting liquid to readily penetrate through its thickness. A suitable topsheet 28 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 28 is typically employed to help isolate the wearer's skin from liquids held in absorbent structure 32.

Various woven and nonwoven fabrics can be used for topsheet 28. For example, the topsheet may be composed of a meltblown or spunbonded web of polyolefin fibers. The topsheet may also be a bonded-carded-web composed of natural and synthetic fibers.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 28 is a nonwoven, spunbond polypropylene fabric composed of about 2.8–3.2 denier fibers formed into a web having a basis weight of about 22 gsm and density of about 0.06 gm/cc. The fabric is surface treated with about 0.28% Triton X-102 surfactant.

In the illustrated embodiment, two containment flaps 62 are connected to the bodyside surface of topsheet layer 28. Suitable constructions and arrangements for containment flaps 62 are described, for example, in U.S. Pat. No. 4,704,116 issued Nov. 3, 1987, to K. Enloe, the disclosure of which is hereby incorporated by reference to the extent that it is consistent herewith.

Containment flaps 62, in the shown arrangement, are attached to topsheet layer 28 along fixed edges 64 of the flaps. A movable edge 66 of each containment flap includes a flap elastic member 68 comprising one or more individual strands of elastomeric material. For example, a plurality of elastic strands may be configured in a spatially separated, generally parallel arrangement, and a suitable elastic strand can, for example, be composed of a 470 decitex "LYCRA" elastomer. Elastic member 68 is connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of topsheet 28 and/or surge management portion 46 toward a generally upright and approximately perpendicular configuration, especially in the crotch section of the diaper. The containment flaps may be constructed of a material which is the same as or different than the material comprising topsheet 28. In optional embodiments, the containment flaps may be constructed of a material which is the same as or different than the material comprising surge management portion 46. The containment flaps may be composed of a material which is air permeable, liquid permeable, substantially liquid impermeable or combinations thereof.

Backsheet 30 may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. Backsheet 30 prevents the exudates contained in absorbent structure 32 from wetting articles such as bedsheets and overgarments which contact diaper 10. The backsheet may be a unitary layer of material or may be a composite layer composed of multiple components assembled side-by-side or laminated.

The shown embodiment of backsheet 30 includes lateral ear sections 29 and 31 of waistband portions 12 and 14 (FIG. 4), respectively. The ear sections cooperate with the crotch section of backsheet 30 to operably provide leg opening regions for positioning about the legs of the wearer.

In particular embodiments of the invention, backsheet 30 is a polyethylene film having a thickness of from about 0.012 millimeters (0.5 mil) to about 0.051 millimeters (2.0 mils). In the shown embodiment, the backsheet is a film having a thickness of about 1.25 mil. Alternative constructions of the backsheet may comprise a woven or nonwoven fibrous web layer which has been totally or partially constructed or treated to impart the desired levels of liquid impermeability to selected regions that are adjacent or proximate the absorbent body.

In a particular aspect of the invention, a terminal edge of the substantially liquid impermeable backsheet material extends to a position which is substantially coterminous with a front or rear waistband edge of the backsheet member. In the illustrated embodiment, for example, a polymer film comprising backsheet 30 extends to a position which is substantially coterminous with a front or rear waistband edge of the backsheet.

Backsheet 30 typically provides the outer cover of the article. Optionally, the article may comprise one or more separate layers which are in addition to the backsheet and are interposed between the backsheet and the absorbent structure.

Backsheet 30 may optionally be composed of a microporous, "breathable" material which permits water vapor to escape from absorbent structure 32 while still preventing liquid exudates from passing through the backsheet. For example, the breathable backsheet may be composed of a microporous polymer film or a nonwoven fabric which has been coated or otherwise treated to impart a desired level of liquid impermeability. An example of a suitable microporous film is a PMP-1 material, which is available from Mitsui Toatsu Chemicals, Inc., a company having offices in Tokyo, Japan; or an XKO-8044 polyolefin film available from 3M Company of Minneapolis, Minnesota. The backsheet can also be embossed or otherwise be provided with a matte finish to exhibit a more aesthetically pleasing appearance.

The size of backsheet 30 is typically determined by the size and shape of absorbent structure 32 and the exact diaper design selected. Backsheet 30, for example, may have a generally T-shape, a generally I-shape or a modified hourglass shape, and may extend beyond the terminal edges of absorbent structure 32 by a selected distance to provide side and end margins.

Topsheet 28 and backsheet 30 are connected or otherwise associated together in an operable manner. As used therein, the term "associated" encompasses configurations in which topsheet 28 is directly joined to backsheet 30 by affixing topsheet 28 directly to backsheet 30, and configurations wherein topsheet 28 is joined to backsheet 30 by affixing topsheet 28 to intermediate members which in turn are affixed to backsheet 30. Topsheet 28 and backsheet 30 can be affixed directly to each other in the diaper periphery 18 by attachment means (not shown) such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix topsheet 28 to backsheet 30. The above-described attachment means may also be employed to interconnect and assemble together the other component parts of the article.

Fastening means, such as tape tab fasteners 36, are typically applied at the lateral, side ends of the back waistband region 14 of diaper 10 to provide a mechanism for holding the diaper about the waist of the wearer in a conventional manner. Tape tab fasteners 36 can be any of those well known in the art, and are typically applied to the corners of diaper 10. Suitable, refastenable adhesive tape fasteners are described in U.S. Pat. No. 5,147,347 issued Sep. 15, 1992 to Y. Huang et al. (Attorney Docket No. 9871), the disclosure of which is hereby incorporated by reference to the extent that it is consistent herewith. Alternatively, other types of fastening means, such as snaps, pins, belts, hooks, buckles, "hook/mushroom"-and-loop fasteners (e.g. VELCRO fasteners) and the like, may be employed.

Elastic members 34 and 82 are disposed adjacent periphery 18 of diaper 10. Along each side edge region 20, leg elastic members 34 are arranged to draw and hold diaper 10 against the legs of the wearer. Waist elastic members, such as rear waist elastic 82, may also be disposed adjacent either or both of the end edges 22 of diaper 10 to provide elasticized waistbands.

Elastic members 34 and 82 are secured to diaper 10 in an elastically contractible condition so that in a normal understrain configuration, the elastic members effectively contract against diaper 10. The elastic members can be secured in an elastically contractible condition in at least two ways, for example, the elastic members may be stretched and secured while diaper 10 is in an uncontracted condition. Alternatively, diaper 10 may be contracted, for example, by pleating, and the elastic members secured and connected to diaper 10 while the elastic members are in their unrelaxed or unstretched condition. Still other means, such as heat-shrink elastic material, may be used to gather the garment.

In the embodiment illustrated in FIG. 1, leg elastic members 34 extend essentially along the complete length of crotch region 16 of diaper 10. Alternatively, elastic members 34 may extend the entire length of diaper 10, or any other length suitable providing the arrangement of elastically contractible lines desired for the particular diaper design.

Elastic members 34 and 82 may have any of a multitude of configurations. For example, the width of the individual elastic members 34 may be varied from 0.25 millimeters (0.01 inches) to 25 millimeters (1.0 inches) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 10 with sprayed or swirled patterns of hotmelt adhesive.

In the illustrated embodiments of the invention, leg elastic members 34 may comprise a carrier sheet 37 to which are attached a grouped set of elastics composed of a plurality of individual elastic strands 39. The elastic strands may intersect or be interconnected, or be entirely separated from each other. The shown carrier sheet may, for example, comprise a 0.002 cm thick film of unembossed polypropylene material. The shown elastic strands can, for example, be composed of "LYCRA" elastomer available from DuPont, a business having offices in Wilmington, Del. Each elastic strand is typically within the range of about 620–1050 decitex (dtx), and preferably, is about 940 dtx in an embodiment of the invention wherein three, generally parallel strands are employed for each elasticized legband.

Leg elastics 34 may be generally straight or optionally curved. For example, the curved elastics can be inwardly bowed toward the longitudinal centerline of the diaper with the innermost point (or apex, relative to the cross-direction of the article) of the set of curved elastic strands positioned approximately 0.75–1.5 inches inward from the outer most edge of the set of elastic strands. In particular arrangements, the curvature of the elastics may not be configured or positioned symmetrically relative to the lateral centerline of the diaper. As representatively shown in FIG. 9, for example, the curved elastics may have an inwardly bowed and outwardly bowed, reflex-type of curvature, and the length-wise center of the elastics may be offset by a selected distance within the range of about 0–8 cm toward either the front or rear waistband of the diaper to provide desired fit and appearance. In particular embodiments of the invention, the innermost point (apex) of the set of curved elastics can be offset about 0–12 cm towards the front or rear waistband of the diaper, and the outwardly bowed reflexed-portion can be positioned toward the diaper front waistband.

Figure 9:
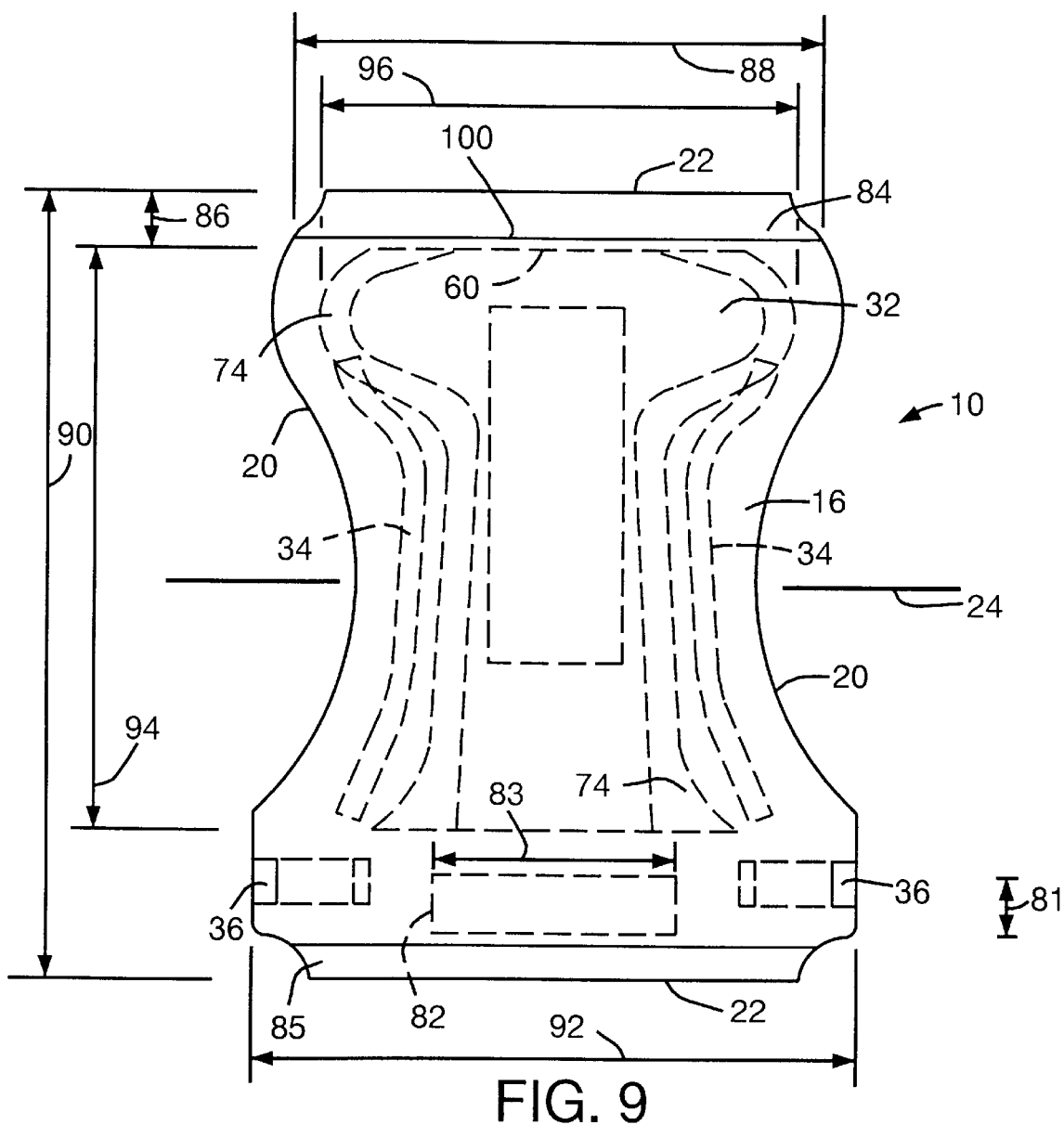
FIG. 9 representatively shows a plan view of a diaper article of the invention viewed from its outerside.

The shown embodiment of the invention includes a single waist elastic member 82 located at rear waistband portion 14 of diaper 10. In optional configurations of the invention, a second waist elastic member may be positioned at front waistband portion 12. With reference to FIGS. 1 and 9, waist elastic 82 is positioned in the rear end margin 22 provided by backsheet 30, and is located in a substantially co-linear, cross-directional alignment with the shown pair of fastener tabs 36. Such alignment can provide improved stretchability and flexibility along ear sections 31 and along the rear waistband region of backsheet 30.

Waist elastic member 82 has a cross-directional width dimension 83 which can extend substantially 100% of the width of the diaper rear waistband. Optionally the width of the waist elastic is within the range of about 20–80 percent of article width 92. Preferably, the waist elastic width dimension is within the range of about 25–60 percent of article width 92, and more preferably, is within the range of about 40–50 percent of the article width. In the various aspects of the invention, waist elastic 82 has a cross-directional width dimension within the range of about 5–33 centimeters. Preferably, the cross-dimensional width dimension of the waist elastic is within the range of about 10–20 centimeters, and more preferably is within the range of about 12–16 centimeters. In the aspects of the invention configured for a newborn infant, waist elastic 82 can have a cross-directional width dimension within the range of about 5–20 centimeters. Preferably, the cross-dimensional width dimension of the waist elastic is within the range of about 6.5–15 centimeters, and more preferably is within the range of about 10–13 centimeters.

In the various aspects of the invention, waist elastic 82 can also have a length dimension 81 which is not less than about 1 centimeter, preferably is not less than about 2 cm, and more preferably is not less than about 2.5 cm. In particular configurations, the length dimension of waist elastic 82 is not more than about 10 cm, preferably is not more than about 8 cm, and more preferably, is not more than about 5 cm.

Waist elastic member 82 may be composed of any suitable, natural or synthetic elastomeric material. The waist elastic member may also be configured as a film, single or multiple strips, parallel or nonparallel strands, or any other desired configuration. In a particular aspect of the invention, elastic member 82 can comprise an elastomeric, cloth-like nonwoven fibrous material, such as an elastomeric stretch-bonded laminate (SBL) web or an elastomeric meltblown web.

Examples of suitable meltblown elastomeric fibrous webs for forming waist elastic 82 are described in U.S. Pat. No. 4,663,220 issued May 5, 1987, to T. Wisneski, et al., the disclosure of which is hereby incorporated by reference to the extent that it is consistent with the present description. Examples of composite fabrics comprising at least one layer of nonwoven textile fabric secured to a fibrous elastic layer are described in European Patent Application EPA 0 110 010 published Apr. 8, 1987, with the inventors listed as J. Taylor et al., the disclosure of which is hereby incorporated by reference to the extent that it is consistent herewith. The composite nonwoven fabrics are commonly referred to as stretch-bonded laminates.

In yet another aspect of the invention, elastic member 82 can be composed of an elastomeric, stretchable composite web comprising individual, discrete strips of elastomeric material secured to one or more nonwoven fibrous layers. Such a composite web may, for example, comprise an elastomeric meltblown material arranged in a selected pattern of strips and suitably sandwiched and attached between two layers of nonwoven, spunbonded fibrous material. The composite web may alternatively comprise a selected pattern of individual elastomeric strips operably secured to a nonwoven fibrous layer or between two nonwoven layers. The elastomer strips may, for example, be composed of a thermoplastic, melt extrudable material. Examples of suitable elastomer materials include polyether-polyamide block copolymers, polyurethanes, synthetic linear A-B-A and A-B block copolymers, chlorinated rubber/EVA (ethylene-vinyl acetate) blends, EPDM (ethylenepropylene diene monomer) rubbers, EPM (ethylene-propylene monomer) rubbers, blends of EPDM/EPM/EVA, and the like.

An absorbent body, such as absorbent structure 32, is positioned between topsheet 28 and backsheet 30 to form diaper 10. The absorbent body has a construction which is generally compressible, conformable, non-irritating to the wearer's skin, and includes a retention portion 48 which is capable of absorbing and retaining liquid body exudates. It should be understood that, for purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

Figure 7:
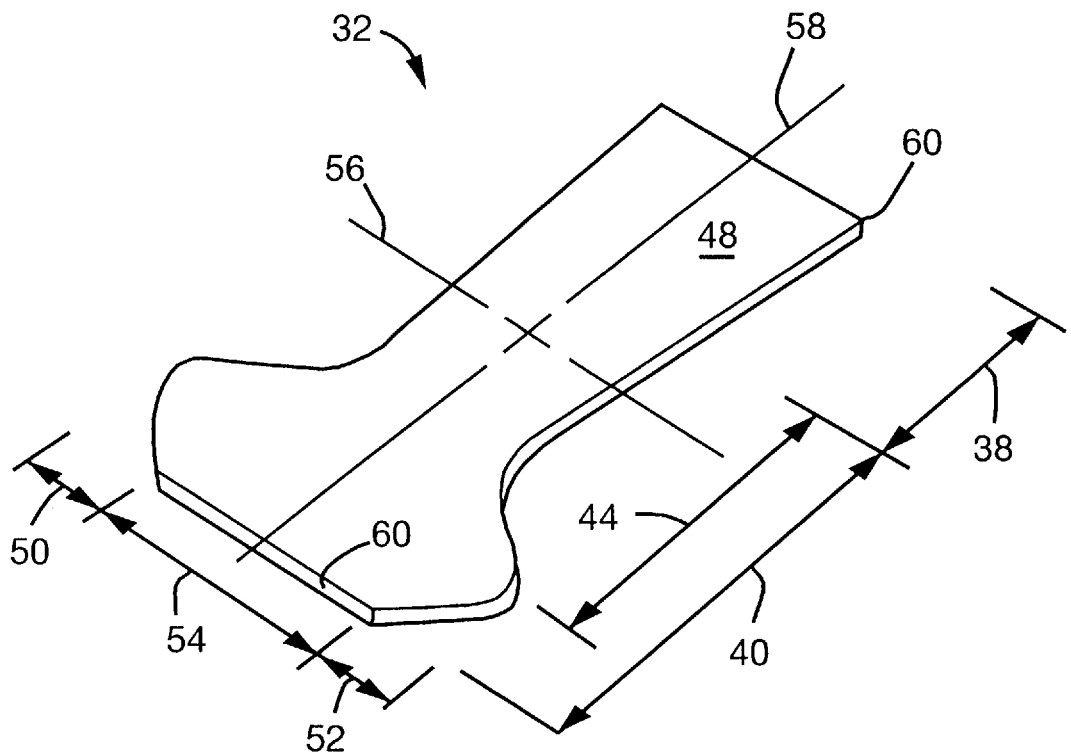
FIG. 7 generally shows an absorbent structure having a retention portion.

In the embodiment representatively shown in FIG. 7, absorbent structure 32 generally includes a back section 38 and a front section 40, and provides a liquid acquisition, target zone 44. The absorbent structure has end edges 60 and a contoured, curvilinear periphery, particularly along its side edges. The two generally mirror-image, inwardly bowed, lateral edges provide for a narrower intermediate section suitable for positioning in the crotch of the wearer.

In the representatively shown embodiment of absorbent structure 32, front section 40 can be conceptually divided into three regions comprising two transversely spaced ear regions 50 and 52 respectively, and a central region 54. The front portion 40 includes at least a portion of target zone 44, and can be constructed to encompass all of the target zone 44 of absorbent structure 32.

Target zone 44 encompasses the area where repeated liquid surges typically occur in absorbent structure 32. Generally stated, the target zone is a section of absorbent structure 32 which is located in the front 60% of the length of absorbent structure. With reference to the percentage of the total length 94 of absorbent structure 32 measured into absorbent structure from the front waistband edge thereof, the target zone may preferably comprise a region which begins at a line positioned approximately 10% of the absorbent structure length away from the front waistband edge and ends at approximately 60% of the absorbent structure length away from the front waistband edge.

The ear regions 50 and 52 comprise portions which generally extend from the lateral side edges of the absorbent structure toward longitudinal center line 58 a distance from one-tenth to one-third of the overall width of absorbent structure 32, and connect to central region 54. When the diaper is worn, the ear regions are configured to generally engage the sides of the wearer's waist and torso, and central region 54 is configured to generally engage the medial portion of the wearer's waist and torso.

With respect to absorbent articles, wherein reduced bulk or reduced cost may be important, the surge management and retention portions need not extend over the entire, overall shape of the garment. In the shown aspects of the invention, for example, absorbent structure 32 can include a retention portion 48 which has a length 94 which is not less than about 40 percent of article length 90. Preferably, the retention portion has a length 94 which is not less than about 50 percent of article length 90, and more preferably, has a length which is not less than about 60 percent of the article length to better provide desired benefits. In particular aspects of the invention, the retention portion has a length 94 which is not more than about 90 percent of article length 90. Preferably, the retention portion has a length 94 which is not more than about 80 percent of article length 90, and more preferably has a length which is not more than about 70 percent of the article length to better provide desired benefits. In particular aspects of the invention, the absorbent body structure, particularly retention portion 48, can be asymmetrically located along the length of the article delimited by backsheet 30. In the illustrated embodiment, for example, at least about 45 percent of the retention portion length 94 is located in a front half-section 25 of diaper 10 and/or backsheet 30 (FIG. 9). Other aspects of the invention have at least about 55 percent of the retention portion length is located in the front half-section of the article. Preferably, at least about 60 percent of the retention portion length is located in the front half-section of the article, and more preferably, at least about 65 percent of the retention portion length is located in the front half-section of the article to provide desired absorbent performance.

In the illustrated embodiments of the invention, liquid-permeable wrap sheet layer 70 is approximately the same length as retention portion 48. In other aspects of the invention, however, absorbent structure 32 can include a wrap sheet layer 70 having a length which is longer than the length of retention portion 48. For example, the wrap sheet layer may be about 10–30 percent longer than the length of the retention portion.

Where wrapsheet 70 is longer than retention portion 48, the retention portion can be asymmetrically located along the length of the wrapsheet. For example, at least about 55 percent of the retention portion length 94 can be located in a front, half-length of wrapsheet 70. Preferably, at least about 65 percent of the retention portion length is located in the front half-section of wrapsheet 70, and more preferably, at least about 75 percent of the retention portion length is located in the front half-section of the wrapsheet to provide desired benefits.

Absorbent structure 32 may be manufactured in a wide variety of sizes and shapes (for example, rectangular, trapezoidal, T-shape, I-shape, hourglass shape, etc.) and from a wide variety of materials. The size and the absorbent capacity of absorbent structure 32 should be compatible with the size of the intended wearer and the liquid loading imparted by the intended use of the absorbent article. Further, the size and the absorbent capacity of absorbent structure 32 can be varied to accommodate wearers ranging from infants through adults. In addition, it has been found that with the present invention, the densities and/or basis weights of the respective surge management 46 and retention 48 portions, as well as their relative ratios, can be varied.

In a particular aspect of the invention, the absorbent structure has an absorbent capacity of at least about 200 gm of synthetic urine. Other arrangements of the absorbent structure can have an absorbent capacity of at least about 300 gm or of at least about 400 gm of synthetic urine to provide desired performance.

Various types of wettable, hydrophilic fibrous material can be used to form the component parts of absorbent structure 32. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials used for the surge management portion 46 can be provided by a Cahn SFA-222 Surface Force Analyzer System. When measured with this system in accordance with the procedure described in detail herein below, fibers having contact angles less than 90° are designated "wettable", while fibers having contact angles greater than 90° are designated "nonwettable".

At least a portion of retention portion 48 can be situated in target zone 44, and the retention portion may substantially define the boundaries of absorbent structure 32. Retention portion 48 can comprise a matrix of hydrophilic fibers, such as a web of cellulosic fluff, mixed with particles of high-absorbency material. In particular arrangements, retention portion 48 may comprise a mixture of superabsorbent hydrogel-forming particles and synthetic polymer melt-blown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent structure and relatively higher concentrations toward the outerside of the absorbent structure. Suitable z-gradient configurations are described in U.S. Pat. No. 4,699,823 issued Oct. 13, 1987 to Kellenberger et al., the disclosure of which is incorporated herein by reference to the extent that it is consistent with the present description.

The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly (acrylic acid) and poly (methacrylic acid), poly (acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent structure include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarson et al. in U.S. Pat. No. 3,902,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in retention portion 48 is generally in the form of discrete particles. The particles can be of any desired shape, for example, spiral or semispiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in retention portion 48.

Preferred for use are particles having an average size of from about 20 microns to about 1 millimeter. "Particle size" as used herein means the weighted average of the smallest dimension of the individual particles.

In a particular aspect of the invention, absorbent retention portion 48 comprises a matrix of substantially hydrophilic fibers having a quantity of high-absorbency material distributed therein. Selected superabsorbent polymers having improved absorbent properties can be important for maximizing the performance while retaining the desired thinness of the absorbent article. To provide improved performance, the particles of superabsorbent material can be selected to provide an absorbency-under-load (AUL) value which is within the range of about 25–40, and provide a Absorbent Capacity (AC) value which is within the range of about 32–48. The rate of liquid uptake by the superabsorbent material is within the range of about 3–15 g/g (grams liquid per gram superabsorbent) at 30 seconds of absorbency under load, 6.5–21 g/g at 5 minutes absorbency under load and 25–40 g/g at 60 minutes absorbency under load.

A suitable method for determining AUL is described in detail in U.S. patent application Ser. No. 184,302 of S. Kellenberger and entitled "Absorbent Products Containing Hydrogels with Ability to Swell Against Pressure" (Attorney Docket No. 8786); European Patent Application EP 0 339 461 A1, published Nov. 2, 1989; the disclosure of which is hereby incorporated by reference to the extent that it is consistent with the present specification.

An example of superabsorbent polymer suitable for use in the present invention is SANWET IM 3900 polymer available from Hoechst Celanese, a business having offices in Portsmouth, Va. Other suitable superabsorbents may include W45926 polymer obtained from Stockhausen, a business having offices in Greensboro, N.C.

The matrix of hydrophilic fibers comprising retention portion 48 may be a layer of cellulosic wood pulp fluff, and the particles of superabsorbent polymer can be distributed within the matrix of hydrophilic fibers. The hydrophilic fibers and high-absorbency particles are provided in a fiber-to-particle ratio which is not more than about 75:25, preferably is not more than about 70:30 and more preferably is not more than about 55:45, by weight. In further aspects of the invention, the fiber-to-particle ratio is not less than about 25:75, preferably is not less than about 30:70 and more preferably is not less than about 45:55, by weight. Such fiber-to-particle ratios can be particularly desireable in the target zone of the absorbent structure. In the illustrated embodiment, for example, the fiber-to-particle weight ratio is not more than about 60:40 and is not less than about 40:60 to provide desired performance.

The hydrophilic fibers and high-absorbency particles form an average composite basis weight which is within the range of about 400–900 gsm. Again, such basis weight is particularly desireable in the target zone of the absorbent structure. In certain aspects of the invention, the average composite basis weight is within the range of about 500–800 gsm, and preferably is within the range of about 550–750 gsm to provide desired performance.

To provide the desired thinness dimension to the absorbent article, retention portion 48 is configured with a thickness which is not more than about 0.6 cm. Preferably, the thickness is not more than about 0.53 cm, and more preferably is not more than about 0.5 cm to provide improved benefits. For the purposes of the present invention, the thickness is determined under a restraining pressure of 0.2 psi (1.38 kPa).

The density of retention portion 48 or other component of the absorbent article can be calculated from its basis weight and thickness. With respect to diapers, for example, the weight and thickness are measured on newly unpacked, unfolded and dry diapers at a restraining pressure of 0.2 psi (1.38 kPa). For measuring thickness, a suitable device is a TMI foam thickness gauge, Model No. TM1-49-21 or its equivalent. The apparatus is available from Testing Machines, Inc. of Amityville, N.Y.

In the various embodiments of the invention, absorbent retention portion 48 includes 4–22 grams of wood pulp fluff. In the embodiment configured for a newborn infant, the retention portion can include about 4–9 grams of fluff to provide desired benefits. The wood pulp fluff generally provides shape and form to diaper 10, and carries and positions the particles of superabsorbent polymer or other high-absorbency material. Retention portion 48 can contain about 2–12 grams of superabsorbent polymer, and in an embodiment configured for newborn infants, can contain about 4.5 grams of superabsorbent polymer. Sufficient superabsorbent polymer is incorporated into retention portion 48 to provide an adequate total absorbent capacity of at least about 200 gm of urine. For example, a newborn-size diaper for an infant weighing about 5–10 lb can typically have a total retention capacity of about 250 gm of urine. A medium size diaper for an infant weighing about 13–23 lb can typically have a total retention capacity of about 500 grams of urine.

The fluff and superabsorbent particles can be selectively placed into desired zones of retention portion 48. For example, the fluff basis weight may vary across the width dimension of retention portion 48. Alternatively, relatively larger amounts of fluff may be positioned toward the front waistband end of the retention portion. For example, see U.S. Pat. No. 4,585,448 issued Apr. 29, 1986, to K. Enloe. In the illustrated embodiment, the majority of the superabsorbent material is distributed down a medial region of retention portion 48 which extends along the length dimension of the retention portion and measures about 3.5–4.5 inches in width. In addition, the superabsorbent material may have a selected zoned placement to reduce the amount of superabsorbent material located proximate the side and end edges of the retention portion. The reduced amounts of superabsorbent material at the edges of the retention portion can improve the containment of the superabsorbent particles within the fibrous fluff matrix of retention portion 48. The pulsed, zoned placement of the superabsorbent material can, for example, be achieved by the method and apparatus described in copending U.S. patent application Ser. No. 07/462,363 of C. Pieper et al. filed Jan. 9, 1990, and entitled "Method and Apparatus for Intermittently Depositing Particulate Material in a Substrate" (Attorney Docket No. 8761), the disclosure of which is hereby incorporated by reference to the extent that it is consistent herewith.

In a particular aspect of the invention, absorbent structure 32 is generally T-shaped with the laterally extending crossbar of the "T" generally corresponding to the front waistband portion of the absorbent article for improved performance, especially for male infants. In the embodiments sized for a newborn infant, for example, the retention portion across the ear section of the front waistband region of the article has a cross-directional width of about 7.0 inches, the narrowest portion of the crotch section has a width of about 2.6 inches and the back waistband region has a width of about 3.2 inches.

Figure 4:
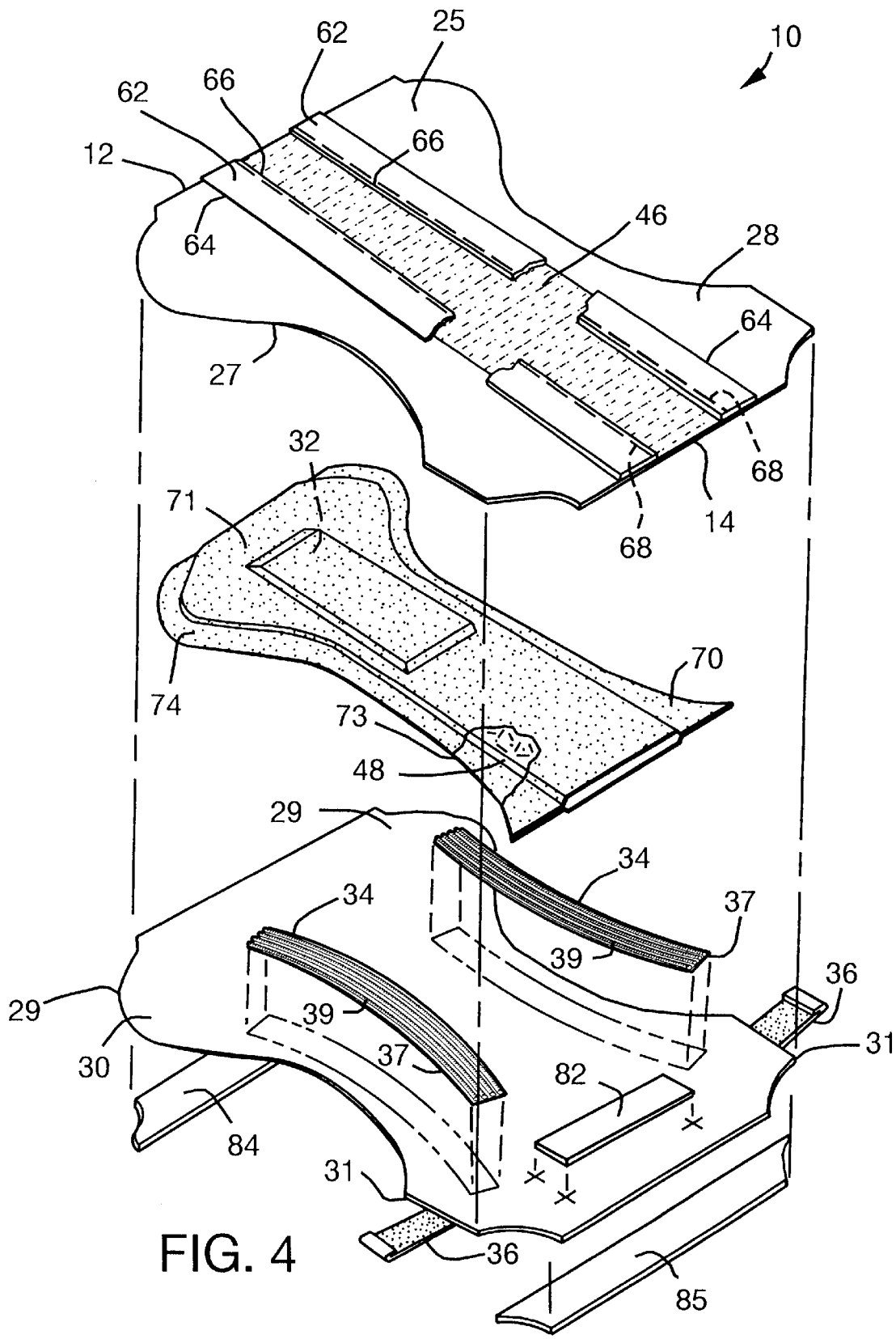
FIG. 4 representatively shows an exploded perspective view of a diaper article of the invention having a surge layer on the bodyside surface of the topsheet.
Figure 5:
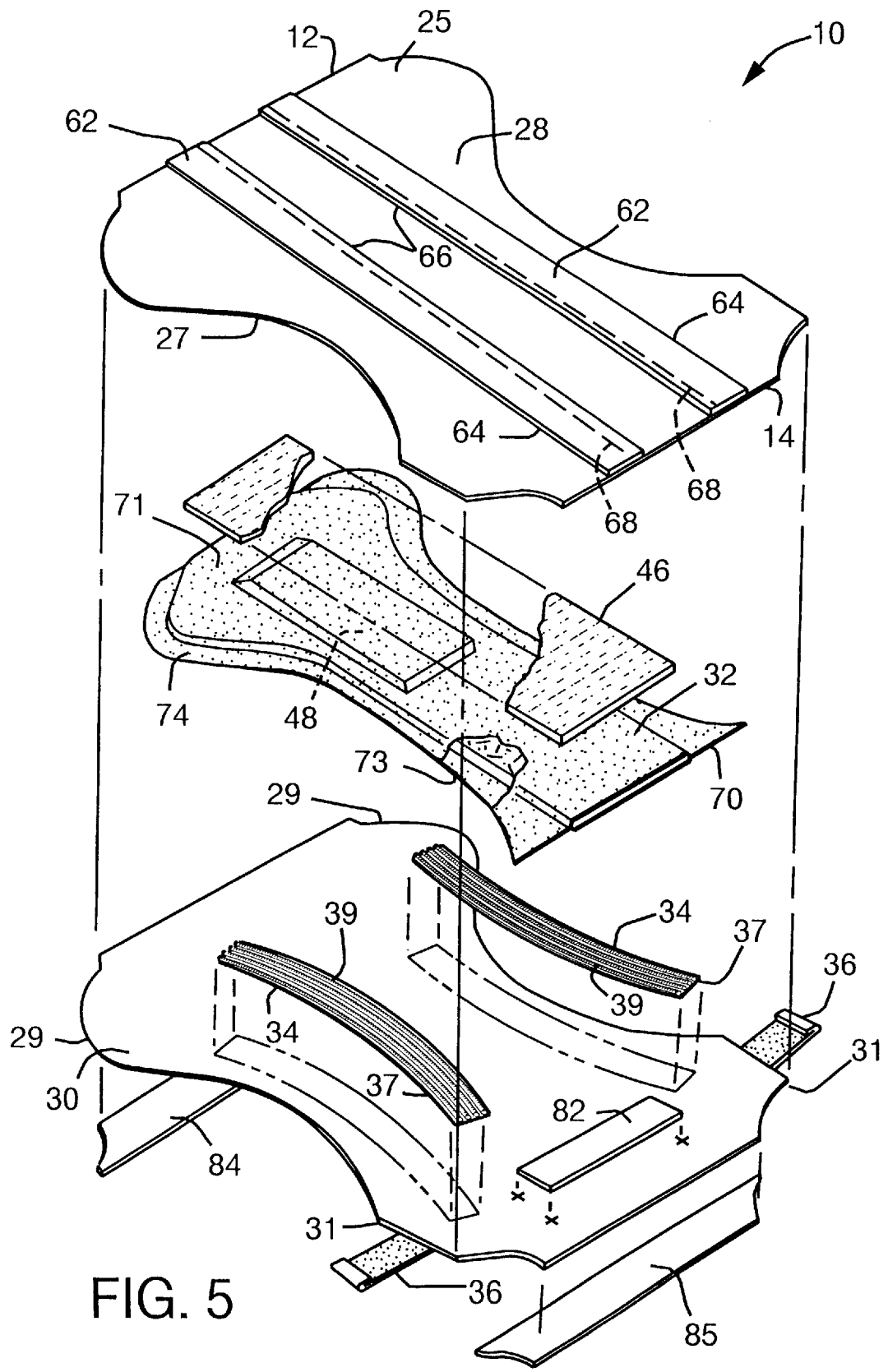
FIG. 5 representatively shows an exploded perspective view of another embodiment of a diaper article of the invention having a surge layer on the outerside surface of the topsheet.
Figure 8:
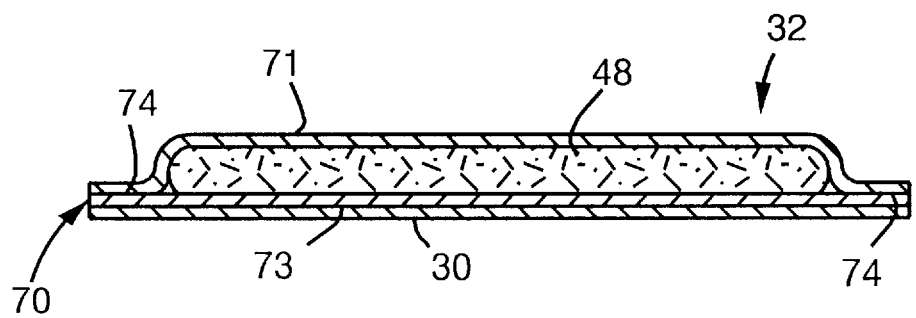
FIG. 8 representatively shows a cross-sectional view of an absorbent structure having a multi-component tissue wrap.

With reference to FIGS. 4 and 8, the entire absorbent structure 32, or any individual portion thereof, such as the retention portion, can be overwrapped in a hydrophilic high wet-strength envelope web, such as a high wet-strength tissue or a synthetic fibrous web. Such overwrapping web can also increase the in-use integrity of the absorbent structure. The web can be suitably bonded, such as with adhesive, to absorbent structure 32 and to other components of the product construction.

Due to the high concentrations of superabsorbent particles, or other high-absorbency material, in retention portion 48, there can be an increased difficulty with regard to containing the high-absorbency particles within the retention portion and restricting the movement or migration of the superabsorbent onto the bodyside of the diaper. To improve the containment of the high-absorbency material, absorbent structure 32 can include an improved overwrap, such as wrap sheet 70, placed immediately adjacent and around retention portion 48. The wrap sheet is preferably a layer of absorbent material which covers the major bodyside and outerside surfaces of the retention portion, and preferably encloses substantially all of the peripheral edges of the retention portion to form a substantially complete envelope thereabout. Alternatively, the wrap sheet can provide an absorbent wrap which covers the major bodyside and outerside surfaces of the retention portion, and encloses substantially only the lateral side edges of the retention portion. Accordingly, both the linear and the inwardly curved portions of the lateral side edges of the wrap sheet would be closed about the retention portion. In such an arrangement, however, the end edges of the wrap sheet may not be completely closed around the end edges 60 of the retention portion at the waistband regions of the article.

At least the bodyside layer of wrap sheet 70 has a pore distribution wherein no more than about 5 percent of the pores, as measured by Coulter porometry, are greater than about 50 micrometers in diameter. For example, the complete wrap sheet 70, or at least the bodyside layer of the wrap sheet, may comprise a meltblown web composed of meltblown polypropylene fibers having a fiber size of about 5 micrometers and arranged to form a basis weight within the range of about 8–20 gsm. Another example of absorbent wrap 70 may comprise a low porosity cellulosic tissue web composed of an approximately 50/50 blend of hardwood/softwood fibers. The tissue can have a 13 lb basis weight at the reel and a porosity of about 90 cfs/sq. ft.

Absorbent wrap 70 may comprise a multi-element wrapsheet which includes a separate bodyside wrap layer 71 and a separate outerside wrap layer 73, each of which extends past all or some of the peripheral edges of retention portion 48, as representatively shown in FIG. 8. Such a configuration of the wrap sheet can, for example, facilitate the formation of a substantially complete sealing and closure around the peripheral edges of retention portion 48. In the back waistband portion of the illustrated diaper, the absorbent wrap may also be configured to extend an increased distance away from the periphery of the retention portion to add opacity and strength to the back ear sections of the diaper. In the illustrated embodiment, the bodyside and outerside layers of absorbent wrap 70 extend at least about ½ inch beyond the peripheral edges of the retention portion to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 70 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

To provide the bonding between the bodyside and outerside portions of absorbent wrap 70, an adhesive, such as National Starch 72-3723 adhesive, can be printed onto the appointed bonding areas 74 of the absorbent wrap with, for example, a rotogravure-type system. The adhesive is available from National Starch and Chemical Co., a business having offices in Bridgewater, N.J., and rotogravure-type adhesive applicators are available from Egan Machinery Division, a business having offices at Oconto Falls, Wis. Retention portion 48 can then be placed between the bodyside and outerside portions of absorbent wrap 70 and the mating edges of the absorbent wrap portions can be bonded together to provide a generally complete peripheral seal along substantially the entire perimeter of retention portion 48. In the illustrated embodiment, the adhesive is applied at an add-on rate of about 5 grams of solids per square meter of bonding to attach together the lapping edges of the bodyside and outerside portions of absorbent wrap 70.

With alternative arrangements having an absorbent wrap composed of a nonwoven meltblown fibrous web, the peripheral sealing of the bodyside and outerside wrap layers may be accomplished by employing hot calendering to provide a sealed strip region around the periphery of the retention portion. For example, absorbent wrap 70 may comprise a first nonwoven layer of meltblown fibers positioned adjacent the bodyside of retention portion 48, and a second meltblown fibrous layer positioned adjacent an outerside of the retention portion. The contacting portions of the first and second meltblown fabrics are thermally bonded around the periphery of the retention portion employing an intermittent, discontinuous thermal bonding pattern, such as a shaped-dot pattern. Such a bonding pattern can provide a labyrinth-type seal which can more effectively inhibit undesired movements of the high-absorbency particles without excessively stiffening the bonded area. The thermal bonding process can employ an unheated anvil roll and a heated pattern roll, which is heated to a temperature of about 250° C. The resultant thermal bonding may be accomplished at speeds of up to 990 feet/second.

Due to the thinness of retention portion 48 and the high superabsorbent concentrations within the retention portion, the liquid uptake rates of the retention portion, by itself, may be too low, or may not be adequately sustained over three insults of liquid into the absorbent structure. The addition of a layer of surge management material into the absorbent structure, however, can advantageously improve the overall uptake rate of the composite absorbent structure. Surge management portion 46 is typically less hydrophilic than retention portion 48, and has an operable level of density and basis weight to quickly collect and temporarily hold liquid surges, and to transport the liquid from its initial entrance point to other parts of the absorbent structure 32, particularly retention portion 48. This configuration can help prevent the liquid from pooling and collecting on the portion of the absorbent garment positioned against the wearer's skin, thereby reducing the feeling of wetness by the wearer.

Various woven and nonwoven fabrics can be used to construct surge management portion 46. For example, the surge management portion may be a layer composed of a meltblown or spunbonded web of polyolefin fibers. The surge management layer may also be a bonded-carded-web composed of natural and synthetic fibers. The surge management portion may be composed of a substantially hydrophobic material, and the hydrophobic material may optionally be treated with a surfactant or otherwise processed to impart a desired level of wettability and hydrophilicity.

In addition, the surge management layer can be configured with an average bulk density which is not more than about 0.10 g/cc (determined at 0.2 psi). Preferably, the bulk density of the surge management layer is within the range of about 0.02–0.06 g/cc to provide improved effectiveness. The types of nonwoven materials that may be employed include powder-bonded-carded webs, infrared bonded carded webs, and through-air-bonded-carded webs. The infrared and through-air bonded carded webs can optionally include a mixture of different fibers, and the fiber lengths within a selected fabric web may be within the range of about 1.0–3.0 inch.

Surge management portion 46 can have a generally uniform thickness and cross-sectional area. Alternatively, a configuration can be employed wherein the bodyside surface area of the surge management portion is greater or less than the surface area of a section taken along an X-Y plane located below the bodyside surface of the surge management portion.

With reference again to FIGS. 1 and 4, the absorbent article represented by diaper 10 can generally comprise a liquid surge management portion 46 and an absorbent retention portion 48 adjacently arranged in liquid communication with the surge management portion. As representatively shown in FIG. 5, surge management portion 46 may alternatively be placed immediately adjacent absorbent structure 32 to provide a substantially direct contact between the surge management portion and the retention portion of the article.

In the various embodiments of the invention, at least a part of surge management portion 46 is located within the target zone 44 of absorbent structure 32, and preferably, the surge management portion has an areal extent which extends completely over target zone 44. Retention portion 48 is positioned in liquid communication with surge management portion 46 to receive liquids released from the surge management portion, and to hold and store the liquid. In the shown embodiments, surge management portion 46 comprises a separate layer which is positioned over another, separate layer comprising the retention portion, thereby forming a dual-layer arrangement. The surge management portion serves to quickly collect and temporarily hold discharged liquids, to transport such liquids from the point of initial contact and spread the liquid to other parts of the surge management portion, and then to eventually release such liquids into the layer or layers comprising retention portion 48.

In the shown embodiment, the layer comprising the surge management portion is substantially free of absorbent gelling material. Surge management portion 46 may, optionally, contain a small amount of particulate gelling material to help acquire an initial liquid surge, but the amount should not be excessive. When excessive amounts of particulate absorbent gelling material are maintained in the surge management portion, the particles can cause the target zone to retain and hold unacceptably high amounts of the liquid. In addition, the transport of liquids away from target zone 44 to other sections of absorbent structure 32, particularly retention portion 48, can be undesirably impaired.

As mentioned previously, surge layer 46 can be a separately formed layer, which lies adjacent the outerwardly facing surface of topsheet 28 between the retention portion and topsheet. Thus, surge management portion 46 need not extend through the entire thickness of absorbent structure 32. The retention portion can optionally include a recess area which wholly or partially surrounds surge management portion 46, or the retention portion can be entirely positioned below the surge management portion. The arrangement which includes the recess in retention portion 48 can advantageously increase the area of contact and liquid communication between the retention portion and surge management portion. It should be understood, however, that surge management portion 46 could optionally be constructed to extend through the entire thickness of absorbent structure 32 so that the capillary flow of liquid into retention portion 48 occurs primarily in the generally sideways (X-Y) direction.

A capillary force differential can be provided at the interface between the retention portion 48 and the material immediately adjacent the bodyside of the retention portion to improve the containment characteristics of absorbent structure 32. For example, if the surge management portion is composed of layer 46 positioned immediately adjacent to the retention portion, and if the surge layer is appropriately configured to provide and maintain a relatively lower capillary attraction, as compared to the capillary attraction exhibited by retention portion 48, then liquid surges occurring in target zone 44 tend to be desorbed more readily from the surge management portion and into the retention portion. Because retention portion 48 can thereby have a relatively higher capillarity than surge management portion 46, the liquid surges tend to be drawn into retention portion 48 and distributed to the more remote regions thereof by wicking along the plane generally defined by the retention portion.

The surge management portion can be of any desired shape consistent with the absorbency requirements of absorbent structure 32. Suitable shapes include for example, circular, rectangular, triangular, trapezoidal, oblong, dog-boned, hourglass-shaped, or oval. Preferred shapes of the surge management portion are those that increase the contacting, liquid communicating surface area between surge management portion 46 and retention portion 48 so that the relative capillarity difference between the portions can be fully utilized. In certain embodiments, such as shown in FIGS. 4 and 5, the surge management portion can be generally rectangular-shaped with a top surface area within the range of about 15–102 $in^2$ (about 97–660 $cm^2$). In the shown embodiment, surge layer 46 has a top surface area of about 45 square inches (about 290 $cm^2$).

In the various embodiments of the invention, such as the arrangement of FIG. 5 where surge management portion 46 is interposed between topsheet 28 and retention portion 48, the surge management portion can comprise a nonwoven fabric which has a basis weight within the range of about 17–102 gsm and includes at least about 25 wt % of bicomponent fibers to provide a desired bicomponent fiber bond-matrix. Up to 100% of the surge fabric can be composed of bicomponent fibers, and accordingly, 0–75 wt % of the fabric may comprise non-bicomponent fibers. In addition, the fabric can comprise a blend of smaller diameter fibers and relatively larger diameter fibers. The smaller sized fibers have a denier of not more than about 3d, and preferably have a denier within the range of about 0.9–3d. The larger sized fibers have a denier of not less than about 3d, and preferably have a denier within the range of about 3–18d. The lengths of the fibers employed in the surge management materials are within the range of about 1–3 in. The bond-matrix and the blend of fiber deniers can advantageously provide for and substantially maintain a desired pore size structure.

For example, the surge management portion may comprise a nonwoven fibrous web which includes about 75 percent polyester fibers of at least 6 denier, such as PET (polyethylene terephthalate) fibers available from Hoechst Celanese. The polyester fibers have a length ranging from about 1.5–2.0 inches in length. The remaining 25 percent of the fibrous web can be composed of bicomponent binder fibers of not more than 3 denier, and preferably about 1.5 denier. The bicomponent fiber length ranges from about 1.5–2 inches. Suitable bicomponent fibers are a wettable, polyethylene/polypropylene bicomponent fiber, available from Chisso, a business having offices located in Osaka, Japan. The bicomponent fiber can be a composite, sheath-core type with the polypropylene forming the core and polyethylene forming the sheath of the composite fiber. The polyester fibers and bicomponent fibers are generally homogeneously blended together and are not in a layered configuration. The fibers can be formed into a carded web which is thermally bonded, such as by through-air bonding or infrared bonding.

As another example, the surge management portion may be composed of a bonded carded web which has a basis weight of about 50 gsm and includes a mixture of polyester (PET) single-component fibers and PET/polyethylene bicomponent fibers. The PET fibers comprise about 60 wt % of the nonwoven fabric, and are about 6 denier with an average fiber length of about 2 in. The PET/polyethylene bicomponent fibers comprise about 40 wt % of the fabric, and are about 1.8 denier with an average fiber length of about 1.5 in. The PET forms the core and the polyethylene forms the sheath of the fiber. In optional constructions, the larger-sized, PET single-component fibers may be replaced by bicomponent fibers. In further optional arrangements, polypropylene/polyethylene bicomponent fibers may be employed to form the bicomponent fiber portion of any of the described fabrics. In addition, the bicomponent fibers may be flat crimped or helically crimped.

Figure 10:
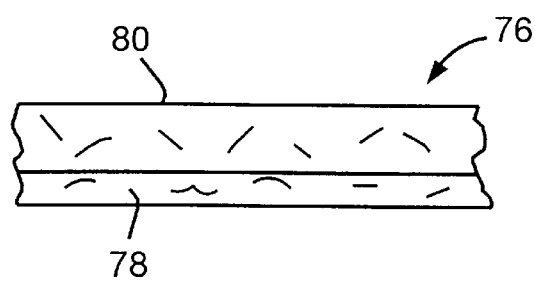
FIG. 10 representatively shows a composite surge management portion.

Referring to FIG. 4, surge management portion 46 can be advantageously configured for placement against the bodyside of topsheet 28. Accordingly, an outerward major surface of the surge management portion would be immediately adjacent and contact the topsheet, and the opposite, innerward major surface of the surge management portion would contact the skin of the wearer. In the shown embodiment, backsheet 30 defines a front waistband section 12, a rear waistband section 14, and an intermediate or crotch section 16 interconnecting the front and rear waistband sections. The backsheet has predetermined width and length dimensions, and an absorbent body 32 is superposed on the backsheet. Topsheet layer 28 is disposed in facing relation with the absorbent body to generally sandwich the absorbent body between the backsheet and topsheet layers, and the topsheet has an appointed outside surface 27 and an appointed bodyside surface 29. A width dimension of topsheet 28 is configured to extend completely over the width of the absorbent body in at least a portion of the crotch section of the absorbent body. With the shown embodiment, the topsheet is also substantially coextensive with the backsheet width over at least a portion of the backsheet crotch section. A surge management portion, such as surge layer 46, is located on the bodyside surface of the topsheet layer, with the surge layer having a width dimension which is less than the width of said topsheet layer.

Where surge management portion 46 is configured for placement adjacent the bodyside of topsheet 28, the surge management portion can be a composite, liner-surge web 76. The composite web includes a bodyside layer portion 80 and an outerside layer portion 78, as representatively shown in FIG. 10. The layer portions can be separately laid and can have different structures and compositions. The fibers within each layer and the intermingling fibers between the layer portions are then suitably interconnected (such as by powder bonding, point bonding, adhesive bonding, latex bonding, or by through-air or infrared thermal bonding) to form a composite web. The resultant composite web has a total basis weight of not more than about 102 gsm. Preferably the total basis weight is within the range of about 24–68 gsm, and more preferably is within the range of about 45–55 gsm. In addition, the total average density of the composite web is not more than about 0.10 g/cc, and preferably is not more than about 0.05 g/cc (as determined at 0.2 psi).

Outerside, surge layer 78 has a basis weight within the range of about 17–50 gsm and includes at least about 25 wt % of bicomponent fibers to provide a desired bicomponent fiber bond-matrix. The outerside layer also comprises a blend of smaller diameter fibers and relatively larger diameter fibers. The smaller sized fibers have a denier within the range of about 0.9–3d, and the larger sized fibers have a denier within the range of about 3–15d. The bond-matrix and the blend of fiber deniers can advantageously provide for and substantially maintain a desired pore size structure within outerside layer 78.

For example, the outerside layer may be composed of a carded web which has a basis weight of about 34 gsm and includes a mixture of polyester (PET) single-component fibers, available from Hoechst-Celanese, and polyethylene/PET (PE/PET) sheath-core bicomponent fibers, available from BASF Corp., Fibers Division, a business having offices in Enka, N.C. The PET fibers can comprise about 60 wt % of the outersided layer and have a denier of about 6 with an average fiber length of about 2 in. The polyethylene/PET bicomponent fibers comprise about 40 wt % of the outerside layer, and have a denier of about 1.8 with an average fiber length of about 1.5 in. Optionally, the larger-sized, PET single-component fibers may be replaced by bicomponent fibers. As a further option, polyethylene/ polypropylene (PE/PP), sheath-core bicomponent fibers may be employed to form the bicomponent fiber portion of any of the described fabrics. Suitable PE/PP bicomponent fibers are available from Chisso Corp., a business having offices in Osaka, Japan.

Bodyside, liner layer 80 includes at least about 90 wt %, and preferably 100 wt %, of bicomponent fibers to provide desired levels of tactile softness and abrasion resistance. The bodyside layer has a basis weight of at least about 10 gsm, and the bicomponent fiber size is within the range of about 0.9–3 denier with a fiber length within the range of about 1–3 in. Preferably, the fiber denier is within the range of about 1.5–2.5, and more preferably, is about 1.8 denier. A preferred fiber length is about 1.5 in. For example, bodyside layer 80 may comprise a carded web which has a basis weight of about 17 gsm and is composed of 100% PET/polyethylene, sheath-core bicomponent fibers, obtained from BASF Corp., with a fiber denier of about 1.8 and fiber lengths of about 1.5 in.

In a particular embodiment of composite surge management portion 76, outerside layer 78 forms approximately 65 weight percent of the composite web and is composed of a blend of polyester fibers and bicomponent fibers. With respect to this blended outerside layer, about 60 weight percent of the blended layer is composed of polyester fibers of at least about 6 denier and with a fiber length within the range of about 1.5–2 inches. The remaining 40 percent of the blended layer is composed of bicomponent fibers of not more than about 3 denier, and preferably about 1.8 denier, with fiber lengths within the range of about 1.5–2 inches. Bodyside layer 80 comprises the remaining 35 weight percent of the composite web, and is composed of bicomponent fibers having a denier within the range of about 0.9–3 to provide a soft liner type material appointed for placement against a wearer's skin. In a particular embodiment, the bodyside layer of the composite web has a basis weight of about 15 gsm and is composed of bicomponent fibers of about 2 denier.

Another embodiment of composite web 76 can comprise a bodyside layer 80 composed of about 100% polyethylene/polyester sheath-core bicomponent fibers of not more than about 3 denier. The bodyside layer has a basis weight of about 15 gsm. In addition, this embodiment of composite web 76 includes an outerside layer composed of a 50/50 blend of polyester fibers of about 6 denier and polyester/polyethylene, sheath-core bicomponent fibers of not more than about 3 denier.

In the various embodiments of the invention, the surge layer width is within the range of about 16–100% of the topsheet width. The surge layer width is preferably at least about 24% of the topsheet width, and more preferably, is at least 50% of the topsheet width to provide desired levels of effectiveness.

The various embodiments of surge management portion 46 may extend over the complete length of retention portion 48, or may extend over only a part of the retention portion length. Where the surge management portion extends only partially along the length of the retention portion, the surge management portion may be selectively positioned anywhere along absorbent structure 32. For example, surge management portion 46 may function more efficiently when it is offset relative to the longitudinal centerline 56 of the absorbent structure toward the front waistband of the garment, and transversely centered within front section 40 of absorbent structure 32. Thus, surge management portion 46 can be approximately centered about the longitudinal center line 58 of absorbent structure 32, and positioned primarily in central region 54 of front section 40 of absorbent structure 32. In the illustrated embodiment, none of surge management portion 46 is located in ear regions of 50 and 52.

The generally forward, offset positioning of surge management portion 46 can be defined by specifying the percentage of the top surface area of surge management portion 46 which is found forward of a particular reference point, such as transverse centerline 24, along the length of absorbent structure 32. The positioning of surge management portion 46 can alternatively be defined with respect to the volume or weight percent of the surge management portion which is positioned forward of a reference point.

The surge management portion and the topsheet layer each have an effective average pore size. In constructions where the surge management portion is located adjacent the outerside of the topsheet, the effective average pore size of the surge management material is preferably smaller than the effective average pore size of said topsheet material, and the material of the surge management portion is preferably more hydrophilic than the topsheet material.

Due to the high concentration of high absorbency material and the thinness of retention portion 48, it has also been desirable to mask the appearance of the soiled absorbent. One arrangement for increased masking is to reduce the light transmission of backsheet 30 to a transmission rate within the range of about 25–40 percent, as measured by a XL 211 Hazegard System (Gardner) available from Pacific Scientific of Silver Springs, Md. or an equivalent measuring device.

For example, the opacity of backsheet 30 may be increased by incorporating $TiO_2$ (titanium dioxide) or other types of pigments into the formulation of a polyethylene backsheet material. In particular arrangements of the invention, backsheet 30 is composed of a polyethylene film having a thickness within the range of about 1.0–2.0 mil.

An alternate arrangement for providing increased masking is to interpose a substantially nonwettable, pigmented web between the retention portion and the backsheet. For example, web may comprise a meltblown web composed of polyolefin fibers pigmented with about 10 weight percent TiO$_2$ pigment. The nonwettable characteristic of web helps reduce the amount of liquid contacting backsheet 30 and thereby helps reduce the visibility of the soiled absorbent.

The absorbent structure of the present invention may advantageously comprise an integrally formed arrangement composed of non-uniform, differentially-configured fibrous sections wherein particular component sections, such as surge management portion 46 and retention portion 48, include fibers which are interwoven or otherwise entangled together at the fibrous interfaces between the components. Such an arrangement can advantageously improve the effectiveness of the liquid transport from the surge management portion and into the retention portion.

With the various embodiments of the invention, the basis weight of surge management portion 46 is at least about 17 grams per square meter (gsm), preferably is at least about 24 gsm, and more preferably is at least about 40 gsm to help provide the total void volume capacity desired for effective operation. In a particular aspect of the invention, the basis weight is within the range of about 17–102 gsm, and preferably, is within the range of about 24–68 gsm to provide further advantages. In a further aspect of the invention, the surge management portion has a basis weight which is within the range of about 40–60 gsm, and preferably, is within the range about 45–55 gsm to provide improved effectiveness. In a particular embodiment, the basis weight is about 50 gsm.

The amount of basis weight can be important for providing a total holding capacity which is adequate to temporarily retain the amount of liquid that is typically discharged by a wearer during a single surge/insult of liquid into the absorbent article. For instance, a basis weight which is too low can result in excessive pooling of liquid against the wearer's skin or excessive run-off of liquid.

It will be readily apparent that absorbent articles requiring more surge capacity may also require proportionally greater amounts of surge management material. The surge management material, however, need not be of uniform basis weight throughout its areal extent, but instead can be arranged so that some sections have more surge management material compared to other sections. For the purposes of the present invention, the effective basis weight will be the weight of the surge management material divided by the area over which the surge management portion extends.

With reference to FIG. 9, an outermost layer of substantially nonwettable, resilient material having the configuration of resilient patch 84 is connected to overlie the outerward surface of the polymer film comprising outer cover 30. Resilient patch 84 is positioned to extend along the front waistband portion of the outer cover, and is arranged to sandwich a preselected section of the polymer film between the topsheet layer and the outermost layer of resilient material. In the illustrated embodiment, the front resilient patch is composed of a material that is substantially non-elastomeric. As a result, the front waistband of diaper 10 is substantially smooth and ungathered.

In optional configurations of the invention, diaper 10 may also include a similar rear patch 85 of resilient material positioned along the laterally extending terminal edge of rear waistband 14. Accordingly in the present specification, the descriptions pertaining to the composition, dimensions, structure and the like of front resilient patch 84 would also apply to rear patch 85, if such a rear patch is incorporated into the article.

Figure 6:
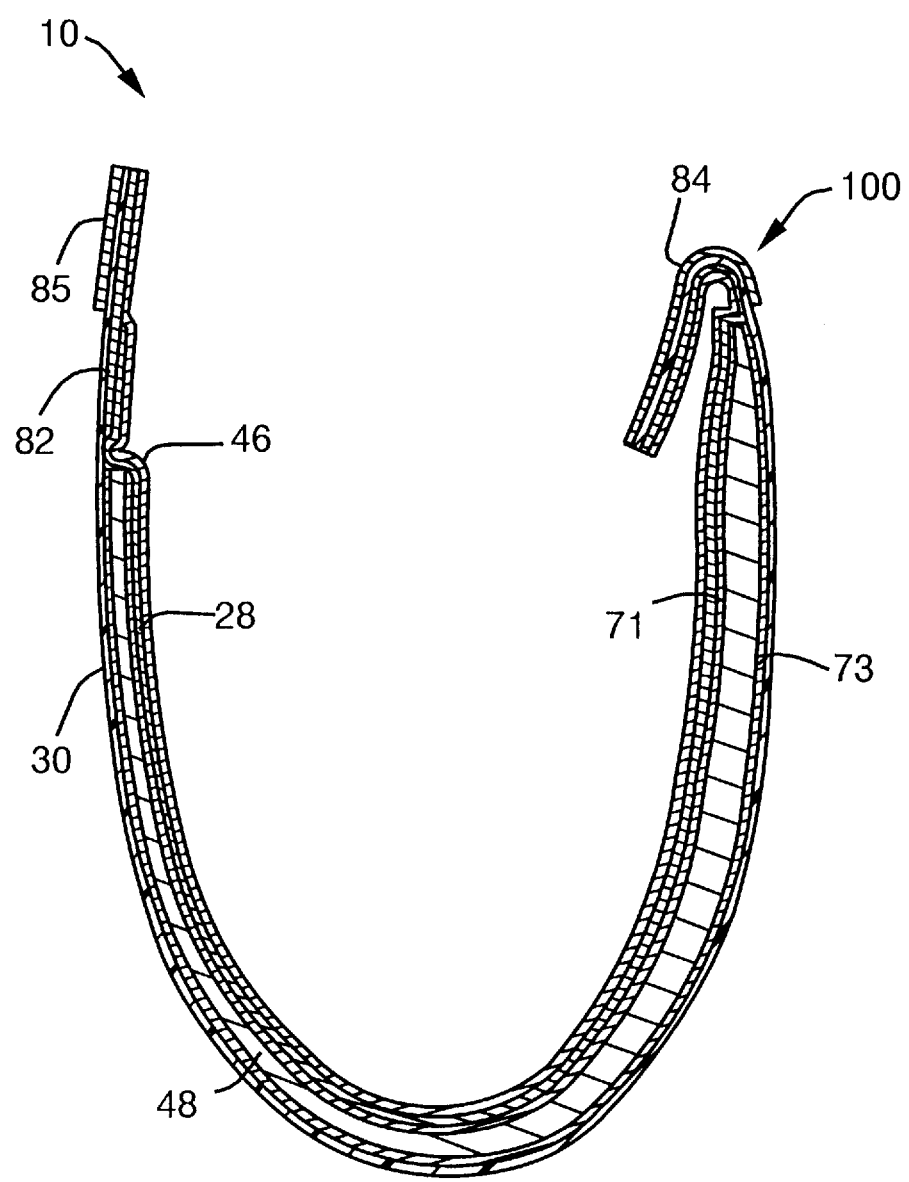
FIG. 6 representatively shows a cross-sectional view of a folded-over front waistband section of a diaper article of the invention.

Resilient patch 84 can effectively define a folding region 100 at the front end margin 22 of the outer cover backsheet. The folding region extends along a cross-direction of backsheet 30 and is appointed to provide for an inward folding of at least a portion of resilient patch 84 for placement against the wearer's skin, as representatively shown in FIG. 6. The areal extent and positioning of the folding region can, for example, be selectively chosen and configured to avoid contacting the front waistband area of the diaper with any residual umbilical cord remaining on a newborn infant.

Referring again to FIG. 9, front patch 84 can be spaced from the laterally extending, terminal edge 60 of absorbent structure 32 by a discrete distance to facilitate the folding operation. In a particular embodiment, for example, the separation distance between the front resilient patch and the absorbent structure can be about 0.25 in (about 0.64 cm).

The nonwettable aspect of resilient patch 84 can advantageously reduce the wicking of liquid, such as urine, when the resilient patch area is inwardly folded over to contact the wearer's skin. As a result the front waistband area can be kept drier and can better avoid overhydrating the portion of the infant's skin that contacts the resilient patch. In addition, when the resilient patch area is inwardly folded, the section of liquid impermeable backsheet material underlying resilient patch 84 is also inwardly folded and provides an effective flap-like dam which can advantageously help to reduce the movement of liquid from absorbent structure 32.

The nonwettable resilient patch may be composed of a woven fabric, a nonwoven fabric material, or a foam material. In the illustrated embodiment, for example, resilient patch 84 is composed of a fibrous, nonwoven material, such as a through-air bonded-carded-web composed of 2.2 dnf polyethylene/polypropylene, sheath-core bicomponent staple fiber. Preferably, the bonded-carded-web is substantially 100% composed of such fiber. In a particular aspect of the invention, the patch material is substantially non-elastomeric and does not generate gathers in the front waistband margin of the article. The absence of gathers in the inwardly-turned, resilient patch can reduce the presence of small channels or gaps leading out of the diaper, and can advantageously help reduce leakage past the front waistband of the diaper.

Resilient patch 84 has a patch length 86 which extends longitudinally of the diaper along not more than about 30 percent of the article length 90, and preferably, extends along not more than about 15 percent of the article length. In further aspects of the invention, patch length 86 can be configured to extend not more than about 10 percent of the article length, and particular aspects of the invention include a resilient patch which extends longitudinally of the diaper along not less than about 2 percent of the article length to provide desired benefits.

Additional aspects of the invention include a resilient patch 84 having a patch length 86 which extends longitudinally of the diaper from the terminal front waistband edge along a distance of not less than about 0.6 cm. Preferably, resilient patch 84 extends longitudinally not less than about 0.8 cm, and more preferably, extends longitudinally not less than about 1 cm to provide desired benefits. In further arrangements, resilient patch 84 has a patch length 86 which extends longitudinally of the diaper from the front waistband edge along a distance of not more than about 3 cm. Preferably, resilient patch 84 extends longitudinally not more than about 5 cm, and more preferably, extends longitudinally not more than about 11 cm to provide desired benefits. In the illustrated embodiments, for example the front resilient patch 84 has a longitudinal extent within the range of about 0.6–11 cm, and preferably, has a longitudinal extent within the range of about 2–2.6 cm. In addition, rear resilient patch 85 has a longitudinal extent within the range of about 0.6–3 cm, and preferably has a longitudinal extent within the range of about 1–1.5 cm.

In yet other aspects of the invention, resilient patch 84 has a cross-directional width 88 which is not less than about 40 percent of article width 92. Preferably, patch width 88 is not less than about 70 percent of the article width, and more preferably, is not less than about 90 percent of the article width. In the illustrated embodiment, for example, patch width 88 can be within the range of about 50–100 percent of the article width 92. In addition, an outermost peripheral edge of resilient patch 84 can be substantially coterminous with the laterally extending, terminal edge of front waistband 12.

Particular aspects of the invention can include a resilient patch 84 having a patch width 88 which extends laterally of the diaper along a distance of not less than about 5 cm, and preferably, extends longitudinally not less than about 10 cm to provide desired benefits. In further arrangements, resilient patch 84 has a patch width 88 which extends laterally of the diaper along a distance of up to about 12 cm. Preferably, resilient patch 84 extends laterally up to about 20 cm, and more preferably, extends laterally up to about 25 cm to provide desired benefits.

The illustrated embodiment of diaper 10, for example, includes both a front resilient patch 84 and a rear resilient patch 85. Each resilient patch has a cross-directional width 88 that extends substantially 100% of the width of the corresponding front and rear waistband edge of the diaper. In addition, the front resilient patch has a longitudinal-direction length 86 of about 0.75 in (about 1.9 cm), and the rear resilient patch has a length of about 0.5 in (about 1.3 cm).

To provide improved softness and comfort, resilient patch 84 has a thickness of at least about 0.025 cm, as measured under a restraining pressure of 0.04 psi (0.28 kPa). Preferably, resilient patch 84 has a thickness of at least about 0.10 cm, and more preferably, has a thickness of at least about 0.15 cm.

In addition, resilient patch 84 can be provided with desired levels of compressibility and resiliency. The material comprising resilient patch 84 can be compressed to a thickness of less than about 50 percent of its original uncompressed thickness when dry and subjected to a compressing pressure of 1 psi (6.89 kPa). In particular aspects of the invention, resilient patch 84 is compressible to a thickness of less than about 45 percent of its original uncompressed thickness, and more preferably is compressible to a thickness of not less than about 40 percent of its original uncompressed thickness. After such compression, resilient patch 84 is also able to recover to at least about 90 percent of its original thickness within 1 minute of the release of the compressing pressure.

To provide improved performance and ease of manufacturing, resilient patch 84 is composed of a material which has a relatively low porosity. In particular aspects of the invention, the material of resilient patch 84 has a porosity of less than about 900 cubic feet per minute per square foot of area (cfm/sf). Preferably, the material of resilient patch 84 has a porosity of less than about 750 cfm/sf, and more preferably, has a porosity of less than about 650 cfm/sf.

In a further aspect of the invention, the material of resilient patch 84 includes an optical brightener, such as UVITEX OB, manufactured by Ciba Geigy Corporation, a company having offices at Ardsley, N.Y. In the illustrated embodiment of the invention, the material of resilient patch 84 includes optical brightener in the amount of at least about 300 parts per million (ppm), as determined by standard gravimetric techniques. Preferably, the optical brightener is in an amount of at least about 250 ppm, and more preferably is in the amount of at least about 100 ppm. In other aspects of the invention, the amount of optical brightener is not more than about 400 ppm, and more preferably, is not more than about 500 ppm to provide improved processing capabilities.

In a particular aspect of the invention, resilient patch 84 (and/or resilient patch 85) is composed of a through-air-bonded web containing 100 percent bicomponent fibers. The bicomponent fibers have a sheath-core construction wherein the sheath is composed of polyethylene and the core is composed of polypropylene. The fibers have a denier within the range of about 1–4 dnf, preferably have a denier within the range of about 1.5–3 dnf, and more preferably have a denier within the range of about 1.8–2.2 dnf. The illustrated embodiment of resilient patch 84 can, for example, be composed of a through-air-bonded carded web composed of 2.2 dnf polypropylene/polyethylene bicomponent fibers available from Hercules, a company having offices located at Wilmington, Del.

In particular aspects of the invention, resilient patch 84 is composed of a fibrous web having a basis weight of not more than about 2.0 ounces per square yard (osy), which is about 68 grams per square meter (gsm). Preferably, the basis weight is not more than about 1.5 osy (about 51 gsm), and more preferably, is not more than about 1.0 osy (about 34 gsm). In other aspects of the invention, resilient patch 84 is composed of a fibrous web having a basis weight of not less than about 0.6 osy (about 20 gsm). Preferably, the basis weight is not less than about 0.7 osy (about 24 gsm), and more preferably is not less than about 0.9 osy (about 30 gsm).

Having thus described the invention in rather full detail, it will be readily apparent that various changes and modifications may be made without departing from the spirit of the invention. All of such changes and modifications are contemplated as being within the scope of the present invention, as defined by the subjoined claims.

We claim:

1. An absorbent article, comprising:

a substantially liquid-impermeable outer cover having a length and a width, said outer cover providing a rear waistband portion and a front waistband portion, and said outer cover having a layer of polymer film material on an outer surface of at least said front waistband portion of said outer cover;

a liquid permeable topsheet layer for contacting a wearer's skin;

an absorbent body interposed between said outer cover and said topsheet layer, said absorbent body having a length and width which are smaller than said outer cover length and width, thereby providing end margins and side margins of said outer cover;

an adhesive fastening means for adhering to said polymer film layer to secure said front and rear waistband portions of said outer cover layer about the wearer;

an elastic member connected to provide elasticized gathers along a cross-direction of said rear waistband portion of said outer cover; and an outermost fibrous layer of substantially nonwettable, resilient, non-elastomeric material connected to overlie said polymer film of said outer cover along said front waistband portion of said outer cover, thereby sandwiching said polymer film between said topsheet layer and said outermost layer of resilient material, said outermost fibrous layer having a lengthwise extent which is less than the length of said outer cover, and said front waistband being substantially ungathered.

2. An article as recited in claim 1, wherein said outermost fibrous layer extends longitudinally along not more than about 20% of said outer cover length.

3. An absorbent article as recited in claim 2, wherein said outermost fibrous layer extends substantially coterminous to a longitudinal terminal edge of said front waistband.

4. An absorbent article as recited in claim 3, wherein said outermost fibrous layer is composed of a material having a fiber denier within the range of about 1–4 dnf.

5. An absorbent article as recited in claim 4, wherein said outermost fibrous layer is composed of a material having a thickness of not less than about 0.025 cm.

6. An absorbent article as recited in claim 5, wherein said outermost fibrous layer is composed of a material having a basis weight of not more than about 68 gsm.

7. An absorbent article as recited in claim 6, wherein said outermost fibrous layer is composed of a material having a basis weight of not less than about 23 gsm.

8. An absorbent article as recited in claim 6, wherein said outermost fibrous layer is composed of a material which can be compressed to a thickness of less than about 50 percent of its original uncompressed thickness when dry and subjected to a compressing pressure of 1 psi (6.89 kPa), and is able to recover to at least about 90 percent of its original thickness within 1 minute of the release of said compression.

9. An absorbent article as recited in claim 8, wherein said outermost fibrous layer extends along a substantially total cross-directional width of said front waistband portion.

10. An absorbent article as recited in claim 6, wherein said front waistband portion of said outer cover is substantially impermeable to air.

11. An absorbent article as recited in claim 10, wherein an edge of said polymer film layer extends to a position substantially coterminous with a waistband edge of said outer cover layer.

12. An absorbent article as recited in claim 6, wherein said outermost fibrous layer defines a folding region which extends along a cross-direction of said outer cover layer and is appointed to provide for an inward folding of at least a portion of said outmost fibrous layer for placement toward the skin of the wearer.

13. An absorbent article as recited in claim 6, wherein said adhesive fastening means is refastenable.

14. An absorbent article as recited in claim 1, wherein said absorbent body is asymmetrically located along said length of said outer cover layer with said absorbent body having at least about 60 percent of a total length of its structure located in a front half-section of said article.

15. An absorbent article as recited in claim 14, wherein at least about 65 percent of said total length of said absorbent body is located in said front half-section of said article.

16. An absorbent article as recited in claim 15, wherein said absorbent body length is not more than about 90% of said length of said outer cover layer.

17. An absorbent article as recited in claim 16, wherein said absorbent body length is not more than about 80% of said length of said outer cover layer.

18. An absorbent article as recited in claim 17, wherein said absorbent body length is not more than about 70% of said length of said outer cover layer.

19. An absorbent article as recited in claim 15, wherein said absorbent body length is not less than about 50% of said length of said outer cover layer.

20. An absorbent article as recited in claim 1, wherein said outermost fibrous layer has a porosity of less than about 900 cfm/sf.

21. An absorbent article as recited in claim 20, wherein said outermost fibrous layer includes an optical brightener in an amount of at least about 100 ppm.

22. An absorbent article as recited in claim 21, wherein said outermost fibrous layer includes an optical brightener in an amount of not more than about 500 ppm.

23. An absorbent article as recited in claim 1, wherein said outermost fibrous layer has a porosity of less than about 750 cfm/sf.

24. An absorbent article as recited in claim 1, wherein said outermost fibrous layer has a porosity of less than about 650 cfm/sf.

25. An absorbent article as recited in claim 1, further comprising another outermost fibrous layer of substantially nonwettable, resilient, non-elastomeric material which is separate from said rear elastic member and is connected to overlie said polymer film of said outer cover along said rear waistband portion of said outer cover, thereby sandwiching said polymer film between said topsheet layer and said outermost layer of resilient material, said outermost fibrous layer having a lengthwise extent which is less than the length of said outer cover.

\* \* \* \* \*